(12) United States Patent
Minow

(10) Patent No.: US 8,764,623 B2
(45) Date of Patent: Jul. 1, 2014

(54) REPRODUCTIVE INFUSION DEVICE

(76) Inventor: Gregory Minow, Chula Vista, CA (US)

(*) Notice: Subject to any disclaimer, the term of this patent is extended or adjusted under 35 U.S.C. 154(b) by 974 days.

(21) Appl. No.: 11/704,091

(22) Filed: Feb. 7, 2007

(65) Prior Publication Data

US 2008/0188708 A1   Aug. 7, 2008

(51) Int. Cl.
*A61B 17/43* (2006.01)

(52) U.S. Cl.
CPC .................................. *A61B 17/43* (2013.01)
USPC .......................................................... 600/35

(58) Field of Classification Search
USPC ............. 600/33–35; 604/347, 349, 317, 327, 604/346, 355; 128/842, 844
See application file for complete search history.

(56) References Cited

U.S. PATENT DOCUMENTS

| | | | | | |
|---|---|---|---|---|---|
| 2,510,249 | A | * | 6/1950 | Penksa | 604/200 |
| 3,401,696 | A | * | 9/1968 | O'Brien | 604/347 |
| 3,781,922 | A | * | 1/1974 | Ericson | 4/144.1 |
| 6,027,443 | A | * | 2/2000 | Nag | 600/33 |
| 6,610,005 | B1 | * | 8/2003 | Tao | 600/34 |
| 2004/0260202 | A1 | * | 12/2004 | McQuaid | 600/573 |

* cited by examiner

*Primary Examiner* — Charles A Marmor, II
*Assistant Examiner* — Carrie R Dorna
(74) *Attorney, Agent, or Firm* — Donn K. Harms

(57) ABSTRACT

A reproductive infusion device for collection of semen for in-home insemination. The device features a collection vessel having a collection cavity defined by a sidewall which communicates through an elongated member extending therefrom. The collection vessel removably engages coaxially with an injection component to transfer collected semen thereto. A plunger engageable with an axial cavity of the injection component is provided for vaginal deposit of collected semen.

14 Claims, 2 Drawing Sheets

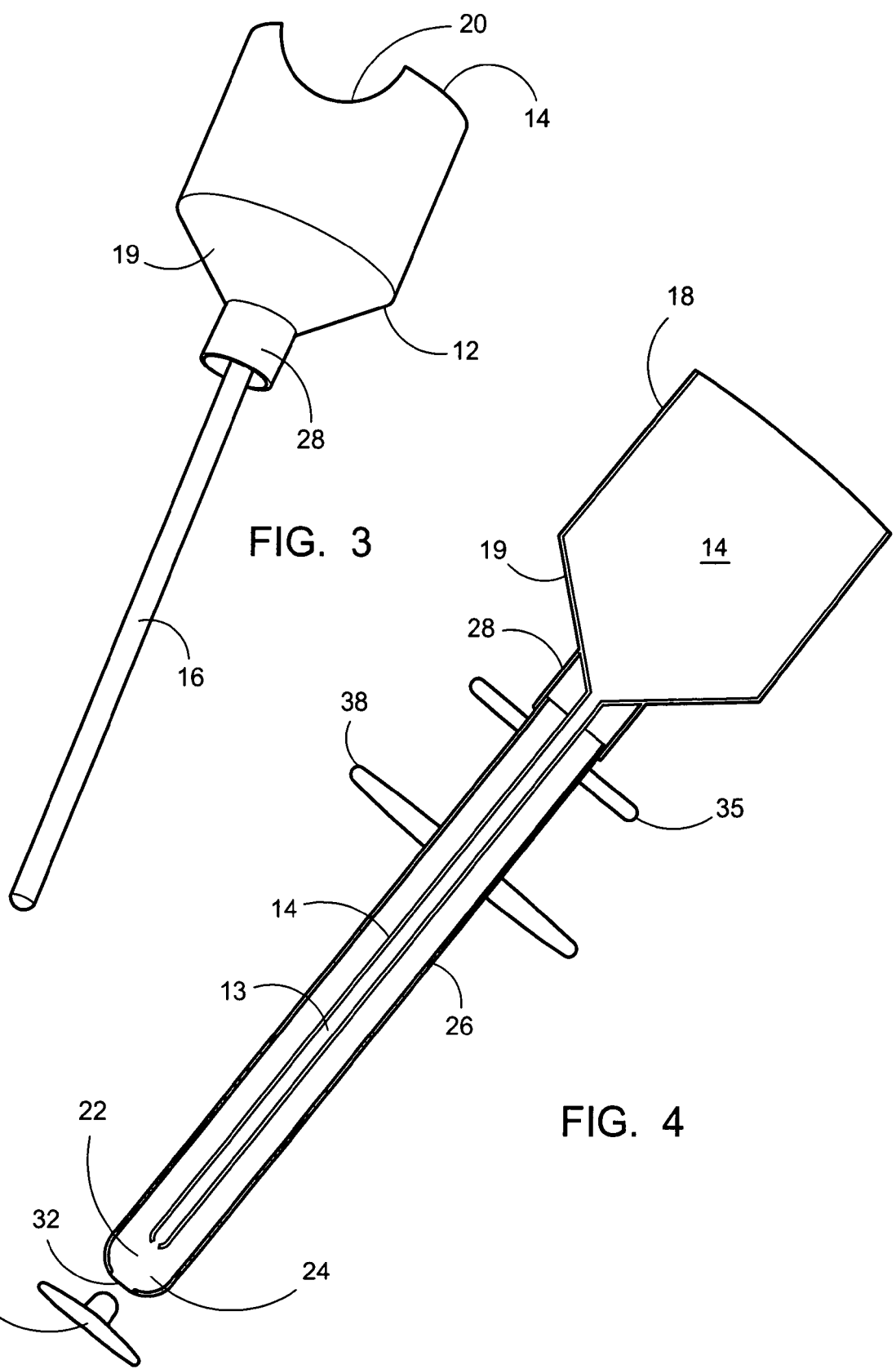

REPRODUCTIVE INFUSION DEVICE

FIELD OF THE INVENTION

The invention herein disclosed and described relates to sexual aids for men. More particularly it relates to a device for easy collection of semen from a male with physical or illness related limitations that prevent or limit intercourse, and deposit thereof in their mate in a manner adapted to achieve pregnancy.

BACKGROUND OF THE INVENTION

As a consequence of spinal injury or illness or paralysis effecting male erection, sexual function is a major concern of men. Men with injuries resulting in paralysis or illness such as multiple sclerosis frequently suffer varying inability to achieve an erection. With this physical limitation men frequently have major emotional concerns as to whether they can father children. Additional emotional concerns arise with such men who may become worried that spouses or potential mates will find them unattractive because their medical condition precludes the fathering of children.

Normally, men have two types of erections. Psychogenic erections result from prurient sights or thoughts and continuation of the ability for this type of erection depends upon the level and extent of paralysis. Men with complete paralysis usually do not have psychogenic erections. A reflex erection occurs involuntarily by direct contact with the penis or other erogenous zones (ears, nipples, neck). Most paralyzed men are able to have a reflex erection unless nerves in the sacral spinal cord (S2-S4) are damaged.

While many men who are paralyzed may be able to achieve a psychogenic erection, due to their physical limitations the erection may not be hard enough or last long enough for successful intercourse. A number of treatments are available for erectile dysfunction such as Viagra (sildenafil), which employ drugs to improves the quality of erections and sexual activity in many paraplegic men. There is some clinical evidence that men with MS also benefit from Viagra.

However, even with erectile dysfunction aids, physical limitations of men with substantial paralysis from spinal injury or from muscle effecting diseases such as MS can still prevent intercourse of a nature that will impregnate their spouse.

Another erection option involves injecting a drug (papaverine or alprostadil) into the shaft of the penis. This produces a hard erection that can last for an hour or more. However, such drugs can result in priapism, a prolonged erection that can damage the penis. Injection erections can also cause bruising, scarring or infection and may not be the best option for those with limited hand function. Further, much like drug aided erections, if the man is physically limited, sufficient intercourse with a spouse to achieve pregnancy can still be a major problem.

Vacuum pumps are a non-invasive, non-drug way to produce an erection, and penile implants are an invasive method of such. However, vacuum induction can cause injury and implants can be uncomfortable and carries a higher risk for complications than other options. The device itself, especially the more complex inflatable units, can malfunction or become damaged. Further, the ability for physical intercourse sufficient in nature to achieve impregnation can still be an overwhelming challenge in cases of MS or certain types of injury inducing paralysis.

Assuming that an erection can be achieved, ejaculation and fertility are also major issues facing men with paralysis or illness. Ejaculation is not always possible, but there are ways to retrieve viable sperm for men suffering from paralysis due to injury or disease. A vibrator is an inexpensive and fairly reliable tool to produce an ejaculation at home or in a clinical setting for most men no matter what the state of their physical illness or injury. In such a procedure the man employs a hand-held vibrator which is held adjacent to one side of the penis. The vibrator works using a simple technique called Transcutaneous Mechanical Nerve Stimulation (TMNS) provided by the vibrator to achieve ejaculation.

However once ejaculated, the collected sperm must still be properly deposited to attempt pregnancy. Between a loving married couple, such a private matter frequently becomes embarrassing by the need to employ doctors and medical personnel in the act of lovemaking to achieve pregnancy. It thus is frequently an overwhelming problem leading to total avoidance of attempting pregnancy for many couples.

As such there exists an unmet need for a device adapted for easy engagement to the male organ during artificial stimulation by a vibrator, which allows for private collection of male ejaculate and subsequent deposit thereof in their mate to attempt impregnation. Such a device should be devoid of potential for physical injury or the need to ingest drugs. Such a device should be easy for even the most physically limited man to engage to the penis during stimulation and collect the ejaculate. Further, such a device should allow for transfer of that collection to other components adapted for insemination of their mate without having to transfer the semen from one container to another. Finally, such a device should be adapted to deposit the sperm in the most appropriate location in the receiving female, to maximize the potential for a successful insemination and pregnancy.

It is an object of this invention to provide a device for the easy collection of ejaculate from erectile dysfunctional men during artificial stimulation.

It is a further object to provide an easy-to-use device that allows for private collection of male ejaculate and subsequent deposit thereof by their mate in an intimate or private setting.

It is an additional object of this invention to provide a device for collection of ejaculate which provides for a stable engagement to the penis during stimulation to aid males who may suffer limited dexterity.

An additional object of this invention is the provision of an ejaculate collection device that allows for direct deposit of the collection into an insemination device.

A further object of the invention is the provision of an ejaculate collection device that allows for individual adjustment of the location of deposit in a receiving female in a manner to accommodate individual physical characteristics and to maximize the potential for a successful insemination and resulting pregnancy.

With respect to the above description and background, before explaining at least one preferred embodiment of the invention in detail, it is to be understood that the invention is not limited in its application to the details of construction and to the arrangement of the components and/or steps set forth in the following description or illustrated in the drawings. The various apparatus and methods of the invention herein described and disclosed are capable of other embodiments and of being practiced and carried out in various ways which will be obvious to those skilled in the art once they review this disclosure. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other devices, methods and systems for carrying out the several purposes of the present disclosed device. It is important, therefore, that the objects and claims be regarded as including such equivalent construction and methodology insofar as they do not depart from the spirit and scope of the present invention.

SUMMARY OF THE INVENTION

The device and method herein disclosed and described provides a plurality of components that operatively engage to collect and deposit semen for men suffering from erectile dysfunction.

The device features a collection vessel having a funnel shaped collection cavity defined by a sidewall in which the recess is located to engage the penis during use. The collection cavity is therefor mechanically engaged to the distal end of the penis during vibratory stimulation such that ejaculate is deposited therein easily. The recess is formed into the sidewall along an upper edge of a sidewall in an arc or half-circle shape in a diameter adapted for engagement with the penis of the man while it is concurrently engaged with a small vibrator device being employed to achieve an ejaculatory response. While the device will function without the recess, it is included in the most preferred mode because the recess allows for an easier engagement with the male organ while the user may be occupied with the proper employment of the vibrator. Additionally, the semi-circular shape provides a means for mechanical engagement with the natural detent at the distal end of the penis to thereby hold it in position during the process for better targeting.

The collection cavity has a slanted or frusto conical lower wall engaged between the sidewall and a communication into an elongated member having an axial conduit communicating between a distal end and the collection cavity. The length of the elongated member is adapted to allow collected ejaculate to flow directly to a lower or distal portion of an axial interior cavity of the injection component which operates similarly to a hypodermic injection device.

Engagement of the collection cavity with the elongated member coaxial in the interior cavity is provided by means for frictional engagement adjacent to the top of the injection component which in the current preferred mode is a collar projecting from the lower wall of the collection cavity. The interior diameter of the collar is adapted for frictional engagement with the upper end of the injection component thereby situating the elongated member substantially coaxially within the elongated internal cavity in the injection component.

By providing the elongated pathway down the axial conduit to route deposited ejaculate only to the lower portion of the injection component, a maximum amount of ejaculate is communicated to a distal end of the internal cavity of the injection component, and air communicated to the injection component below the ejaculate is minimized. This configuration is especially preferred to minimize the amount of air which must be evacuated from the internal cavity and also to minimize the potential for injury to the female receiving the ejaculate which can be caused by air.

In operation, the recess in the collection cavity allows the penis and vibrator combination to move further into the collection cavity than would be possible with a straight edge to the collection cavity and thereby mitigates any possible loss of ejaculate during the initial procedure. Further, the recess provides a temporary mechanical or frictional engagement around the lower half of the circumference of the penis or in the groove located adjacent to the distal end of the human male organ.

With the collection cavity engaged at the upper end of the injection component and the elongated member coaxially within the interior cavity of the injection component, ejaculate collection can begin. A plug is engaged in an aperture communicating with the distal end of the internal cavity to prevent leakage therefrom. Once ejaculation is complete, the injection component is positioned to place the elongated member and coaxially located conduit substantially upright. This allows gravity to progress the ejaculate down the conduit and out the distal end of the conduit into the lower or distal end of the interior cavity of the injection component. This process naturally takes time to allow a capillary action for the ejaculate to proceed to the distal end of the conduit.

During this process the aperture in the distal end of the interior cavity of the injection component is temporarily capped as the ejaculate proceeds to a gravity induced deposit adjacent to the distal end of the collection cavity. A small amount of saline solution may optionally be deposited in the collection cavity to rinse remaining ejaculate into the distal end of the interior cavity. After rinsing, the collection component with the collection cavity is removed by sliding the collar from the injection component and the elongated member out of its coaxial engagement.

Once the injection component is disengaged, with the ejaculate properly positioned at the distal end of the interior cavity, a small plunger is engaged with the interior wall of the interior cavity. At this point in the method, the collection component is rotated to position the distal end upward and the plug in the aperture communicating with the interior cavity at the distal end is removed. In this position, prior to insertion into the female partner, the plunger is depressed until a small bit of liquid bubbles from an aperture at the distal end, thereby effectively removing any of the reduced amount of air that might still remain in the interior cavity.

With the injection component now charged, and after optionally lubricating the distal end of the injection component, it is inserted into the vaginal cavity as close to the opening of the uterus as possible. The length of the collection component is adapted for proper placement and a limiting ring projecting from the exterior of the injection component provides a means to determine insertion length. This ring may be permanently engaged, or in a particularly preferred mode of the device that is adaptable to the wide variances of female anatomy, the ring may be slidably engaged to different positions toward and away from the distal end to adjust insertion length. Locking ridges can also be provided to frictionally engage the ring at various fixed positions. The proper length to maximize changes may be determined by consultation with the female's physician if desired.

Once properly inserted at the desired length, the plunger is slowly depressed into the interior cavity causing the collected ejaculate to be properly deposited in a location optimal to achieve pregnancy just adjacent to the cervix. Once this procedure is finished, the injection component is removed.

The device, being simple to use, maximizing collection potential and also maximizing placement of ejaculate with the female, provides an instrument for loving couples where the male has injury or disease caused erectile dysfunction, to attempt pregnancy in an intimate setting instead of in the clinical setting currently provided. Further, it allows for easy multiple deposits of the ejaculate at times when it has been determined the female may be most likely to conceive.

With respect to the above description of a semen collection and infusion device, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

The foregoing has outlined some of the more pertinent objects of the invention. These objects should be construed to be merely illustrative of some of the more prominent features and applications of the intended invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings wherein the detailed description is for the purpose of fully disclosing the invention without placing limitations thereon.

Figure two is a side view of the device with the collection container removed and a plunger inserted into the internal cavity.

FIG. 3 depicts a perspective view of the collection container with a projecting axial conduit.

Figure 1:
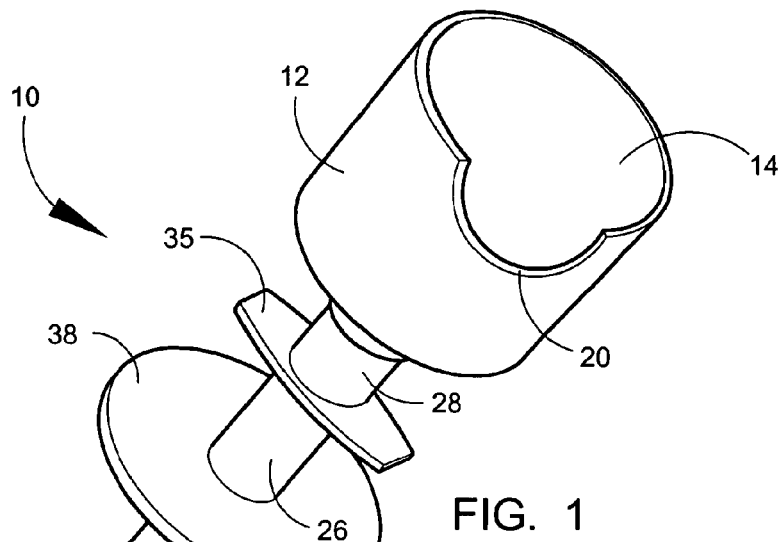
FIG. 1 depicts the device with the collection component engaged to the injection component.
Figure 2:
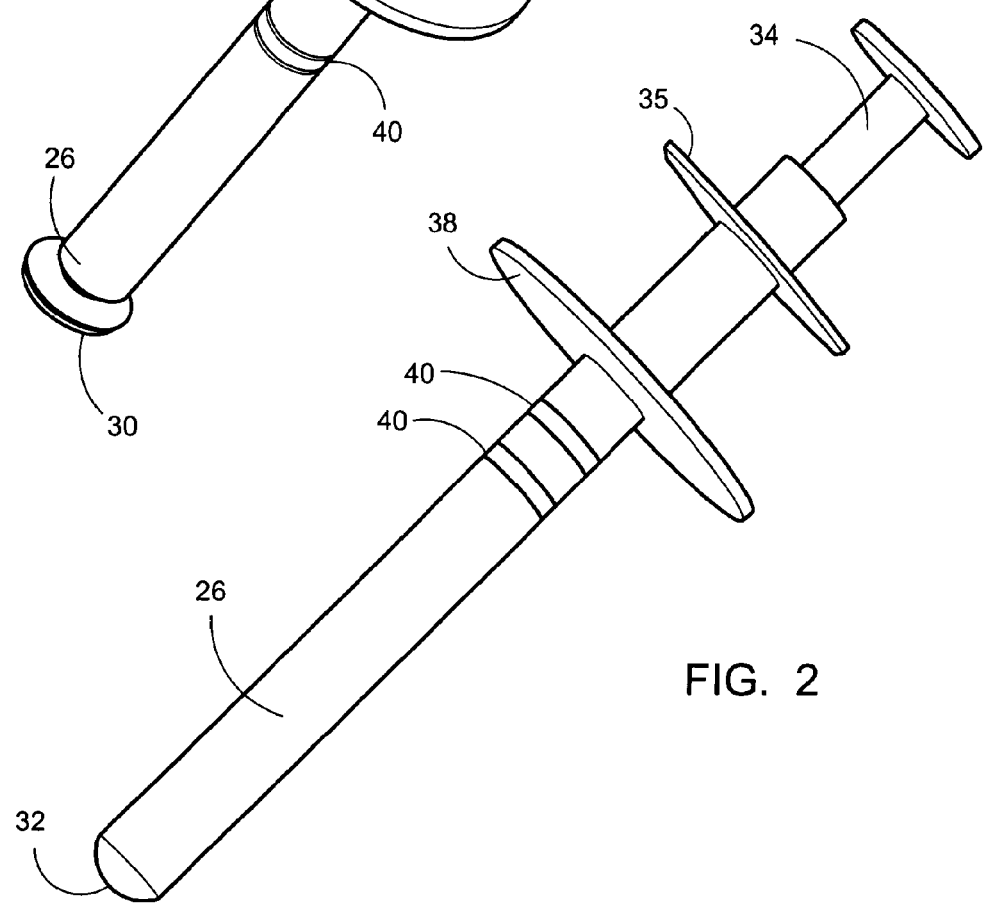

FIG. 4 is a slice through FIG. 1 showing the collection container engaged upon the injection component with the axial conduit coaxial with the internal cavity.

DETAILED DESCRIPTION OF THE PREFERRED EMBODIMENTS OF THE INVENTION

Referring now to the drawings, FIGS. 1-4 depict the disclosed device 10 which features a collection vessel 12 having a collection cavity 14 communicating with the axial passage 13 running the length of an elongated member 16. The collection cavity 14 is defined by a sidewall 18.

The collection cavity 14 in the preferred mode of the device 10 is adapted for a substantially mechanical engagement with the distal end of the penis during vibratory stimulation using the natural shape of the penis to engage with the sidewall 18 and positioning the distal end of the penis pointing into the collection cavity 14. This is preferred because users with moderate or severe dexterity problems caused by injury or illness may have trouble employing the vibrator for stimulation while concurrently trying to aim during discharge.

Currently a recess 20 is formed into the top edge of the sidewall 18 in an arc or half-circle shape and with a diameter adapted for engagement circumferentially with the sulcus or bottom side of the penis during concurrent employment of a small vibrator or other device employed to achieve an ejaculatory response. The half circle shape provides a much larger area for an engagement with the penis than would a straight edge. This recess 20 is well adapted to removably engage with the sulcus of the penis which is the depression naturally occurring adjacent to the head of the penis. When the collection cavity 14 is held at an angle to place the sidewall 18 opposite the recess 20 higher than the distal end of the penis, a means to surround and capture resulting ejaculate is provided, thereby insuring that all ejaculate remains in and is communicated to the bottom of the collection cavity 14. This is especially important since ejection of ejaculate can be at a velocity which would cause the stream to miss the collection cavity 14 were the recess 20 not positioning the distal end the penis below the opposite sidewall 18. Further, by adapting the recess 20 to engage with and around the sulcus or other point on the bottom side of the penis, the user is provided a means to collect ejaculate which requires only one hand to hold the collection vessel 12 which is secure in a removable engagement with the penis. This leaves the other hand of the user free to operate a means to stipulate ejaculation such as a small vibrator.

At a lower end of the collection cavity 14 engaging with the surrounding sidewall 18 is a lower endwall 19 which in the preferred mode is slanted or frusto conical in shape. This shape of the endwall 19 aids in the communication of ejaculate deposited into the collection cavity 14 into the axial passage 13 communicating to the distal end of the elongated member 16. The length of the elongated member 16, as noted, is adapted to allow collected ejaculate to flow directly to a lower or distal portion 22 of a coaxial interior cavity 24 of the injection component 26 of the device 10.

Means for engagement of the collection cavity 14 with the injection component 26, to concurrently locate the elongated member 16 coaxial within the interior cavity 24, in the preferred mode of the device, is provided by a collar 28 projecting from the exterior of the endwall 19 which has a diameter adapted for frictional engagement adjacent to an upper portion of the injection component 26. This provides for an easy engagement and disengagement with the elongated member 16 properly coaxially positioned.

In an engaged position with the collection cavity 14 attached at the upper end of the injection component 26, the process of ejaculate collection in the aforementioned fashion is employed. During the collection process, a plug 30 is engaged in an exit aperture 32 communicating with the distal end of the internal cavity 24 thereby providing a means for temporary sealing the exit aperture 32. Once the collection process is complete and gravity is allowed to move the collection down axial passage 13 and into the distal end of the interior cavity 24, the collection cavity 14 is removed and replaced with a plunger 34 and the device is inverted in position. In the inverted position the plunger 34 may then be depressed by forcing it forward with the thumb while the fingers pull on the grip 35 to remove any air.

As noted, due to the physical characteristics of different women, it is most preferred if the insertion distance of the injection component is made to properly deposit the collection to maximize the potential for pregnancy. An insertion length of the collection component 14 is adapted for proper placement by a limiting ring 38 projecting from the exterior wall surface of the injection component 26 and will prevent insertion past its position and thereby provide a means to determine insertion length. As noted, the limiting ring 38 in the preferred mode is removably engageable to different points along the injection component 26 to allow for adaptability, but could be permanently engaged. If removably engaged, means to determine the length of insertion by mounting the limiting ring 38 in different positions is provided by locking ridges 40 which engage an interior aperture in the limiting ring 38. Other means of mounting the ring 38 can also be employed of course.

Of course once properly configured for insertion to maximize potential results, the device may be employed easily by the mate of the user and the plunger 34 depressed to finish the process to deposit the collection in a location optimum to achieve pregnancy just adjacent to the cervix.

Although the invention has been herein disclosed and described with respect to particular embodiments thereof, it should be realized that various changes and modifications may be made to the produced labels or method of production without departing from the spirit and scope of the invention. While the invention as shown in the drawings and described in detail herein discloses arrangements of elements of particular construction and configuration for illustrating preferred embodiments of structure and method of operation of the present invention, it is to be understood, however, that elements of different construction and configuration and other arrangements thereof, other than those illustrated and described, may be employed in accordance with the spirit of this invention. Any and all such changes, alternations and modifications, as would occur to those skilled in the art, are considered to be within the scope of this invention as broadly defined in the appended claims.

What is claimed is:

1. A reproductive infusion apparatus comprising:
    a collection vessel having a collection cavity defined by a sidewall communicating at a first edge with a bottom wall;
    said sidewall having a distal edge opposite said first edge, said distal edge defining an aperture communicating with said collection cavity;
    an elongated member extending a length from a center portion of said bottom wall to a distal end of said member, said member having an axial cavity communicating between said distal end and said collection cavity;
    an injection component having an axial passageway defined by an interior surface of an elongated component wall, said component wall extending a distance from an intake aperture at a first end to a front wall opposite said intake aperture;
    an exit aperture formed in said front wall, said exit aperture communicating between said axial passageway and the exterior of said injection component; a plug insertable in said exit aperture;
    means for engagement of said collection vessel with said injection component in an engaged position having said elongated member coaxial within said axial passageway;
    a plunger, said plunger engageable with said axial passageway for translational movement between said intake aperture and said front wall; and
    a pathway for semen collected in said collection vessel, said pathway communicating said semen from said collection vessel through said axial cavity to a position adjacent to said front wall of said axial passageway when said collection vessel is in said engaged position with said injection component, whereby said semen collected in said collection vessel and communicated to said axial passageway can be ejected from said exit aperture through a translation of said plunger.

2. The reproductive infusion apparatus of claim 1 additionally comprising:
    a recess formed in said distal edge of said sidewall;
    said recess adapted for an engagement with the sulcus of a penis;
    said engagement providing a capture position to the distal end of the penis lower than a portion of said sidewall positioned opposite said recess, said capture position positioning said sidewall as a shield to prevent ejaculate from overshooting said collection cavity.

3. The reproductive infusion apparatus of claim 2 additionally comprising:
    said engagement allowing for one-handed use of said collection vessel in a secure engagement with said penis.

4. The reproductive infusion apparatus of claim 3 wherein said means for engagement of said collection vessel with said injection component comprises:
    a collar projecting from an exterior surface of said bottom wall in a position surrounding said elongated member;
    said collar having an internal diameter, said internal diameter sized to non-threadably frictionally engage upon an exterior surface of said component wall.

5. The reproductive infusion apparatus of claim 2 wherein said means for engagement of said collection vessel with said injection component comprises:
    a collar projecting from an exterior surface of said bottom wall in a position surrounding said elongated member;
    said collar having an internal diameter, said internal diameter sized to non-threadably frictionally engage upon an exterior surface of said component wall.

6. The reproductive infusion apparatus of claim 5 additionally comprising:
    a limiting member projecting from an exterior surface of said component wall;
    said limiting member defining a leading portion of said component wall between said front wall and said limiting member; and
    said leading portion adapted to define a distance of insertion of said injection component into a vagina.

7. The reproductive infusion apparatus of claim 6 additionally comprising:
    said limiting member projecting from said exterior surface of said component wall from a moveable engagement therewith;
    said limiting member thereby engageable to a plurality of positions between said front wall and said intake aperture; and
    said moveable engagement allowing for adjustment of said distance of insertion.

8. The reproductive infusion apparatus of claim 2 additionally comprising:
    a limiting member projecting from an exterior surface of said component wall;
    said limiting member defining a leading portion of said component wall between said front wall and said limiting member; and
    said leading portion adapted to define a distance of insertion of said injection component into a vagina.

9. The reproductive infusion apparatus of claim 8 additionally comprising:
    said limiting member projecting from said exterior surface of said component wall from a moveable engagement therewith;
    said limiting member thereby engageable to a plurality of positions between said front wall and said intake aperture; and
    said moveable engagement allowing for adjustment of said distance of insertion.

10. The reproductive infusion apparatus of claim 1 wherein said means for engagement of said collection vessel with said injection component comprises:
    a collar projecting from an exterior surface of said bottom wall in a position surrounding said elongated member;
    said collar having an internal diameter, said internal diameter sized to non-threadably frictionally engage upon an exterior surface of said component wall.

11. The reproductive infusion apparatus of claim 1 additionally comprising:
    a limiting member projecting from an exterior surface of said component wall;
    said limiting member defining a leading portion of said component wall between said front wall and said limiting member; and said leading portion adapted to define a distance of insertion of said injection component into a vagina.

12. The reproductive infusion apparatus of claim 11 additionally comprising:
   said limiting member projecting from said exterior surface of said component wall from a moveable engagement therewith;
   said limiting member thereby engageable to a plurality of positions between said front wall and said intake aperture; and
   said moveable engagement allowing for adjustment of said distance of insertion.

13. The reproductive infusion apparatus of claim 1 additionally comprising:
   a grip projecting from an exterior surface of said component wall.

14. A reproductive infusion apparatus comprising:
   a collection vessel having a collection cavity defined by a sidewall communicating at a first edge with a bottom wall;
   said sidewall having a distal edge opposite said first edge, said distal edge defining an aperture communicating with said collection cavity;
   an elongated member extending a length from a center portion of said bottom wall to a distal end of said member, said member having an axial cavity communicating between said distal end and said collection cavity;
   an injection component capable of inseminating a female, said injection component having an axial passageway defined by an interior surface of an elongated component wall, said component wall extending a distance from an intake aperture at a first end to a front wall opposite said intake aperture;
   a limiting member projecting from an exterior surface of said component wall;
   said limiting member defining a leading portion of said component wall between said front wall and said limiting member;
   said leading portion adapted to define a distance of insertion of said injection component into a vagina;
   a grip projecting from an exterior surface of said component wall;
   an exit aperture formed in said front wall, said exit aperture communicating between said axial passageway and the exterior of said injection component; a plug insertable in said exit aperture;
   said collection vessel engagable with said injection component, the engagement characterized by an inner diameter of said collection vessel being in direct non-threaded contact with an exterior surface of said elongated component wall of said injection component, the engagement further characterized by an engaged position having said elongated member coaxial within said axial passageway;
   a plunger, said plunger engageable with said axial passageway for translational movement between said intake aperture and said front wall; and
   a pathway for semen collected in said collection vessel, said pathway communicating said semen from said collection vessel through said axial cavity to a position adjacent to said front wall of said axial passageway when said collection vessel is in said engaged position with said injection component, whereby said semen collected in said collection vessel and communicated to said axial passageway can be ejected from said exit aperture through a translation of said plunger.

* * * * *